(12) United States Patent
MacDougall et al.

(10) Patent No.: US 12,048,508 B2
(45) Date of Patent: Jul. 30, 2024

(54) DIRECT IN-VIVO TUMOR IMAGING USING OPTICAL APPLICATOR

(71) Applicant: Lumeda Inc., Rocky Hill, CT (US)

(72) Inventors: Trevor MacDougall, South Dartmouth, MA (US); Yi Yang, Storrs, CT (US)

( * ) Notice: Subject to any disclaimer, the term of this patent is extended or adjusted under 35 U.S.C. 154(b) by 0 days.

(21) Appl. No.: 18/001,009

(22) PCT Filed: Jun. 8, 2021

(86) PCT No.: PCT/US2021/036282
§ 371 (c)(1),
(2) Date: Dec. 7, 2022

(87) PCT Pub. No.: WO2021/252409
PCT Pub. Date: Dec. 16, 2021

(65) Prior Publication Data
US 2023/0218170 A1  Jul. 13, 2023

Related U.S. Application Data

(60) Provisional application No. 63/036,574, filed on Jun. 9, 2020.

(51) Int. Cl.
*A61B 5/00* (2006.01)
*A61N 5/06* (2006.01)

(52) U.S. Cl.
CPC .......... *A61B 5/0059* (2013.01); *A61N 5/0601* (2013.01); *A61N 2005/063* (2013.01)

(58) Field of Classification Search
CPC .............. A61B 5/0071; A61B 1/00165; A61B 5/0059; G01N 21/64; G01N 21/6402; G01N 21/6228; G01N 21/6456; G01N 21/6486; G01N 2021/6484; G01J 3/4406; G02B 21/0076
See application file for complete search history.

(56) References Cited

U.S. PATENT DOCUMENTS

| | | | |
|---|---|---|---|
| 6,577,391 B1 * | 6/2003 | Faupel | A61B 5/0059 356/337 |
| 2003/0153825 A1 * | 8/2003 | Mooradian | A61B 5/0059 600/407 |
| 2008/0177138 A1 | 7/2008 | Courtney | |
| 2008/0193431 A1 * | 8/2008 | Zheng | A61K 41/0071 424/94.1 |
| 2017/0224257 A1 * | 8/2017 | Rogers | A61B 5/0537 |
| 2018/0055495 A1 * | 3/2018 | Tehrani | A61B 5/0036 |
| 2019/0000320 A1 * | 1/2019 | Anwar | A61B 5/0084 |

* cited by examiner

*Primary Examiner* — Tracie Y Green
*Assistant Examiner* — Michael Chiang
(74) *Attorney, Agent, or Firm* — Matthew J Patterson

(57) ABSTRACT

An interoperative light therapy apparatus and method are disclosed. The apparatus includes an excitation light source, a plurality of light emitting devices and a plurality of light detecting fibers, wherein the plurality of light emitting devices produce a fluorescence light in cancerous cells of a patient treated with a photosensitizing medication. The fluorescence light is collected by the plurality of detector fibers and a digital spatial image of the cancerous cells is produced. The digital spatial image is useful for targeting the cancerous cells in a subsequent resection procedure. An interoperative light therapy apparatus is disclosed that further include a therapy light source that can deliver therapy light to the cancerous cells using the digital spatial image in the subsequent resection procedure.

21 Claims, 2 Drawing Sheets

DIRECT IN-VIVO TUMOR IMAGING USING OPTICAL APPLICATOR

CROSS REFERENCE TO RELATED APPLICATIONS

This application claims the benefit of U.S. Provisional Patent Application Ser. No. 63/036,574 having a filing date of 9 Jun. 2020 as well as Patent Cooperation Treaty Patent Application Serial No. PCT/US2021/036282 filed 8 Jun. 2021. The disclosure of the applications above are incorporated herein by reference in their entirety.

BACKGROUND OF THE DISCLOSURE

Field of the Disclosure

The present disclosure relates to photodynamic therapy.

Description of the Related Art

Light therapy can be used for the treatment of conditions in multiple ways. For example, light therapies involve the delivery of a therapeutic light through a fiber optic device placed proximal to or within a target tumor.

Light therapies can be combined with prior administration of light sensitizing medication (i.e., photosensitizer) that absorbs the therapeutic light and interacts with surrounding tissue constituents (e.g., oxygen) to generate reactive species that can destroy the target tissue. This form of therapy is known as photodynamic therapy ("PDT").

What is needed is a system and method to intraoperatively detect and image cancerous cells.

Summary of the Disclosure

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes claims an optical light delivery system that may include an excitation light source, a plurality of source emitters optically coupled to the excitation light source configured to deliver an excitation light to an area of tissue, a plurality of detector fibers positioned proximate the plurality of source emitters optically coupled to a detector and configured to collect a fluorescence light from at least a portion of the area of tissue, and a microprocessor electronically coupled to the detector and configured to produce an image from the fluorescence light. Other embodiments of this aspect include corresponding computer systems, apparatus, and computer programs recorded on one or more computer storage devices, each configured to perform the actions of the methods.

Implementations may include one or more of the following features. A microprocessor electronically coupled to the detector and configured to produce an image from the fluorescence light. the optical light delivery system may include a display and where the display is configured to present the image to a user. The optical light delivery system may include a flexible optical applicator having a plurality of longitudinal channels positioned therein, where the plurality of source emitters and the plurality of detector fibers are disposed within the plurality of longitudinal channels, and where the flexible optical applicator is configured to be positioned on the area of tissue. The excitation light source is configured to produce the excitation light at a wavelength of about 400 nm. The optical light delivery system where the source emitters are cylindrical light diffusers. The optical light delivery system where the detector fibers may include isotropic probes. The optical light delivery system may include the area of tissue includes a photosensitizing drug and at least a portion of the area of tissue includes a plurality of cancerous cells, and where the excitation light is configured interact with the photosensitizing drug to cause the plurality of cancerous cells to produce the fluorescence light. The optical light delivery system may include a therapy light source optically coupled to the source emitters and configured to produce a therapy light, where the detector fibers are further configured to collect a portion of the therapy light, and a controller configured to control the source emitters to produce an irradiance pattern of the therapy light based on the image.

One general aspect includes an interoperative light therapy method that may include providing a photosensitizing drug to a tissue of a patient, where the photosensitizing drug is configured to concentrate in a presence of cancer in the tissue and where the photosensitizing drug is configured to produce a fluorescence excitation light in a presence of an excitation light, directing the excitation light to a portion of the tissue in a target area of the patient, and detecting a presence or an absence of cancer in the tissue. Other embodiments of this aspect include corresponding computer systems, apparatus, and computer programs recorded on one or more computer storage devices, each configured to perform the actions of the methods.

Implementations may include one or more of the following features. The interoperative light therapy method where the detecting the presence of cancer in a cancerous portion of the tissue may include detecting the fluorescence excitation light and where the detecting the absence of cancer in a healthy portion of the tissue may include detecting the absence of the fluorescence excitation light. The interoperative light therapy method may include producing a digital image of the cancerous portion based on the fluorescence excitation light and the healthy portion based on the absence of the fluorescence excitation light. The interoperative light therapy method may include resecting the cancerous portion using the digital image. The resecting the cancerous portion using the digital image may include configuring the configurable therapy light source to direct a therapy light dosage to the cancerous portion. The interoperative light therapy method may include detecting a subsequent presence or a subsequent absence of cancer in the tissue that may include redirecting the excitation light to the target area of the patient and detecting the subsequent presence of cancer based on the presence of the fluorescence excitation light and detecting the subsequent absence of cancer based on the absence of the fluorescence excitation light. The interoperative light therapy method may include producing a subsequent digital image based on the presence of the fluorescence excitation light and the absence of the fluorescence excitation light.

One general aspect includes an interoperative method of detecting a presence or an absence of cancer in a tissue of a patient that may include providing an excitation light source and a plurality of source emitters optically coupled to the excitation light source and positioning a plurality of detector fibers proximate the plurality of source emitters optically coupled to a detector, providing a microprocessor electronically coupled to the detector and the excitation light source, providing a photosensitizing drug to the tissue, where the photosensitizing drug is configured to concentrate in the presence of cancer in the tissue and where the photosensitizing drug is configured to produce a fluorescence excitation light in the presence of an excitation light, delivering an excitation light from at least one of the plurality of source emitters to an area of the tissue of the patient, detecting the presence of cancer in a cancerous portion of the tissue by collecting the fluorescence excitation light using at least one of the plurality of detector fibers and detecting the absence of cancer in a healthy portion by the absence of collecting the fluorescence excitation light, and producing a digital image using the microprocessor of the cancerous portion based on the fluorescence excitation light and the healthy portion based on the absence of the fluorescence excitation light. Other embodiments of this aspect include corresponding computer systems, apparatus, and computer programs recorded on one or more computer storage devices, each configured to perform the actions of the methods.

Implementations may include one or more of the following features. The interoperative method of detecting a presence or an absence of cancer in a tissue of a patient may include displaying the digital image to a user. The interoperative method of detecting a presence or an absence of cancer in a tissue of a patient includes the excitation light source producing the excitation light at a wavelength of about 400 nm. The interoperative method of detecting a presence or an absence of cancer in a tissue of a patient may include resecting the cancerous portion using the digital image. The resecting the cancerous portion using the digital image may include configuring the configurable therapy light source to direct a therapy light dosage to the cancerous portion. The interoperative method of detecting a presence or an absence of cancer in a tissue of a patient may include detecting a subsequent presence or a subsequent absence of cancer in the tissue that may include redirecting the excitation light to the area of the patient and detecting the subsequent presence of cancer based on the presence of the fluorescence excitation light and detecting the subsequent absence of cancer based on the absence of the fluorescence excitation light. The interoperative method of detecting a presence or an absence of cancer in a tissue of a patient may include producing a subsequent digital image based on the presence of the fluorescence excitation light and the absence of the fluorescence excitation light. The interoperative method of detecting a presence or an absence of cancer in a tissue of a patient may include displaying the digital image to a user. The interoperative method of detecting a presence or an absence of cancer in a tissue of a patient may include providing a flexible optical applicator having a plurality of longitudinal channels positioned therein, disposing the plurality of source emitters and the plurality of detector fibers within the plurality of longitudinal channels, and positioning the flexible optical applicator on the area of the tissue of a patient.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

In the following detailed description of the embodiments, reference is made to the accompanying drawings, which form a part hereof, and within which are shown by way of illustration specific embodiments by which the examples described herein may be practiced. It is to be understood that other embodiments may be utilized and structural changes may be made without departing from the scope of the disclosure.

The present disclosure relates to a system which configured to simultaneously detect abnormal tissue and create an image of a relatively large area where abnormal tissue is suspected. Such a system is useful in the detection of cancerous tumors as well as residual abnormal tissue following surgical resection of a tumor. The present disclosure also includes methods for imaging abnormal (cancerous) tissue and healthy tissue during an intraoperative surgical procedure. In one aspect, the disclosure provides a method for spatially determining tissue heterogeneity and obtaining an in-situ image of the tissue. The image allows for the detection of the presence and location of abnormal tissue as well as absence of abnormal tissue indicating a healthy portion of tissue. Furthermore, the method could entail repeating the imaging and treatment steps until only a portion of the target area indicates abnormal tissue or no abnormal tissue is detected in the patient.

Figure 1:
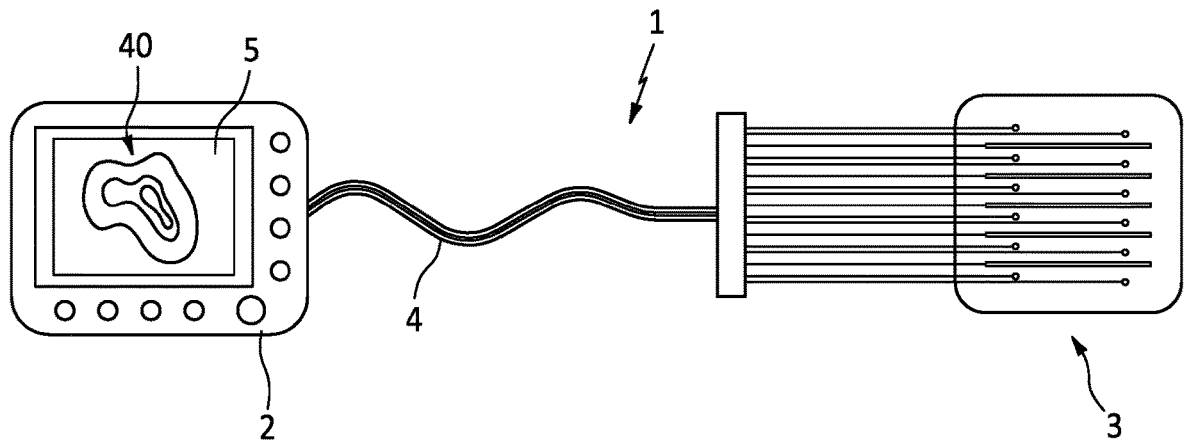
FIG. 1 is a schematic representation of an imaging system in accordance with the present disclosure.

FIG. 1 shows a schematic of one embodiment of imaging system 1 as part of an optical light delivery system. The imaging system 1 is comprised of a number of components including an instrument 2, an optical applicator 3 and a fiber optic tether 4 optically coupling the instrument to the optical applicator via optical connector 6. Instrument 2 includes a configurable therapy light source, an excitation source, a detector, a spectrum analyzer, a controller, a microprocessor and a display 5. The excitation source can comprise a source configured to produce a source light at a wavelength of around 400 nm. The detector can include in a filter configure to block the excitation source wavelength in order to separate the fluorescence wavelengths to be detected. In certain embodiments, imaging system 1 can comprise a PDT system configured to deliver to delivery therapy light in an intraoperative mode with the inventive addition of an excitation source and to configured to deliver an excitation light during an imaging mode. One example of a PDT system is set forth in Patent Cooperation Treaty application number PCT/US21/23176 having a filing date of 19 Mar. 2021, the contents of which are incorporated herein in their entirety.

Figure 2:
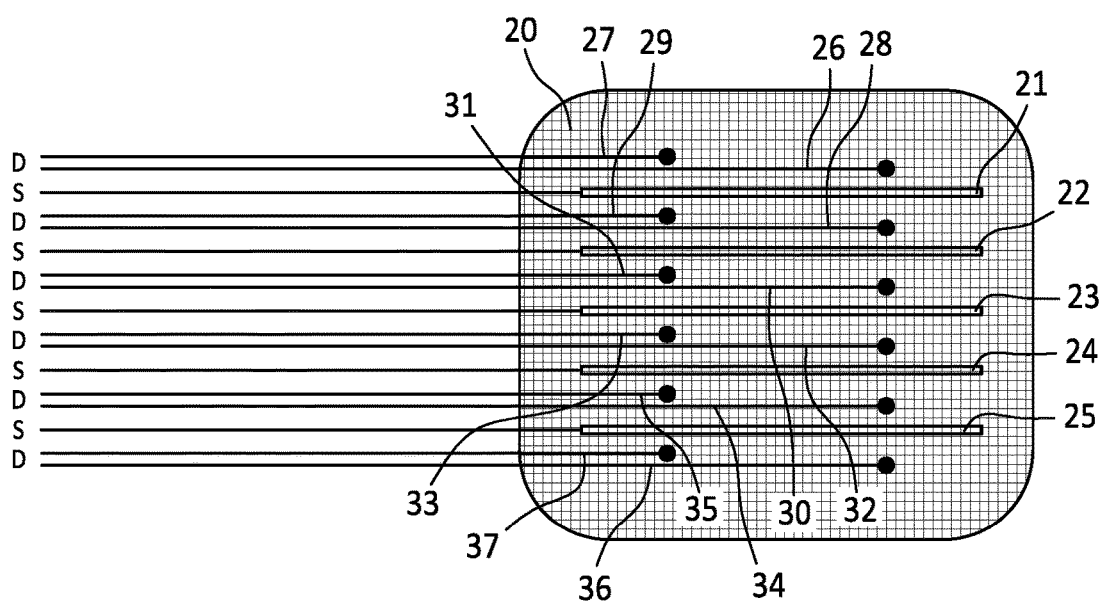
FIG. 2 is a schematic representation showing the detail of an optical applicator in accordance with the present disclosure.

While still referring to FIG. 1 and with reference to FIG. 2, optical applicator 3 is shown in greater detail and is comprised of applicator flap 20, a plurality of source emitters 21-25 CLD'S and a plurality of detection fibers 26-37. In the imaging system 1, excitation light is provided by the excitation source in instrument 1 and delivered to the tissue by source emitters 21-25 and is configured to cause fluorescence excitation as will be disclosed in more detail herein after. Although five source emitters are shown, any number of source emitters can be used without departing from the scope of the present disclosure. Detection fibers 26-37 can comprise point detectors configured to collect the fluorescence excitation and, in some embodiments, can comprise isotropic probe model IP85 available from Medlight S.A. The detection fibers 26-37 are distributed within applicator flap 20 to detect fluorescence excitation from abnormal tissue and to provide an image of the target area as will be disclosed in more detail herein after. It should be appreciated by those skilled in the art that the resolution of imaging system 1 is dependent on the number, placement, and sensitivity of the detection fibers. Fiber optic tether 4 includes individual optical fibers sufficient in number to optically couple to a single one of the detection fibers 26-37 and source emitters 21-25 and can be connected by an optical connector (not shown).

Still referring to FIG. 2, the plurality of source emitters 21-25 can include cylindrical light diffusers disposed on a distal end of each of the source emitters, wherein the cylindrical light diffusers can be positioned inside the channels of an applicator flap 20. One embodiment of a suitable cylindrical light diffuser is model RD-50 available from Rakuten Medical. The plurality of source emitters 21-25 are fixed at predetermined positions within the channels of applicator flap 20. It should be noted that source emitters 21-25 can comprise various lengths of emitters to provide a desired irradiance pattern. Applicator flap 20 can comprise any known flexible applicator flap that is configured to conform to the contours of a human body. Some known applicator flaps include a Freiburg flap manufactured by Elekta and a H.A.M. application available from Mick Radio-Nuclear Instruments. Applicator flap 20 can comprise a flexible pad of silicone rubber that is 8 mm thick and is light transmissive. An array of catheters can be embedded parallel to each other in longitudinal channels therein and in an embodiment are spaced 10 mm apart and to produce a consistent excitation light source-to-tissue distance of about 5 mm. Applicator flap 20 conforms to the shape of surfaces to which it is applied and its positioned remains fixed relative to a target during a procedure even during bodily movements such as breathing and heart beating. Applicator flap 20 can also include embodiments with catheters, alternate materials and custom shapes without departing from the scope of the present disclosure.

It should be appreciated by those skilled in the art that imaging system 1 is useful during an intraoperative surgical procedure such as a photodynamic therapy (PDT) procedure using a therapy light to remove abnormal tissue. In such procedures a photosensitizing drug is typically administered to a patient, which photosensitizing drug is absorbed in higher concentrations in a cancerous portion of tissue. When the cancer cells are exposed to the excitation source, they emit fluorescence excitation light. In some embodiments optical applicator 3 can be positioned over a suspected abnormal tissue target area prior to a surgical procedure to capture an image of the target area such as image 40 in FIG. 3. In some embodiments abnormal tissue, such as a cancerous tumor, can be resected by a surgical procedure or PDT. Optical applicator 3 can then be installed in vivo over the area where the tissue was resected to determine whether any cancerous cells remain. In some instances the flexible optical applicator 3 can be positioned in the pleural space of a patient. If a cancerous portion of tissue remains, fluorescence excitation light collected by any of the detection fibers 26-37 is transmitted back to instrument 2 via optical tether 4 to detector having an opto-electronic converter to convert the light signal to an electronic signal. The electronic signals are processed by the microprocessor in instrument 1 to produce a digital image as well as an image on display 5 of the areas where the fluorescence excitation exists indicating the presence of cancer. Medical personnel can use the image to plan an updated procedure to resect the remaining cancerous tissue. In some embodiments medical personnel can use the configurable therapy light source to deliver therapy light to the areas in the digital image indicating the presence of cancerous tissue and to block therapy light from exposing areas of the image indicating the absence of cancerous tissue (a healthy portion of tissue). In addition, the image can be digitized and matched with a digital image 40 of the tumor prior to surgery, and can be further matched with an image produced from an x-ray. The imaging system 1 can be employed numerous times during the surgical procedure until no fluorescence excitation light is detected indicating the absence of cancer and indicating healthy tissue.

Figure 3:
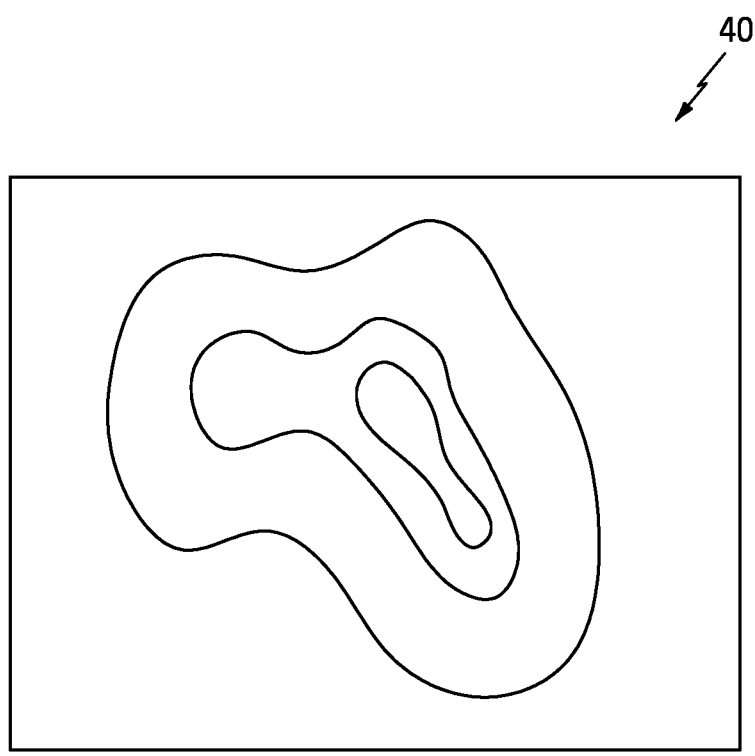
FIG. 3 is an illustration of an image produced with an imaging system of the present disclosure.

In operation, imaging system 1 can be used during an intraoperative surgical procedure. In a surgical procedure for a patient having a cancerous tumor, a photosensitizing drug can be administered prior to surgery. As disclosed herein before, a cancerous portion of tissue absorbs the photosensitizing drug in higher concentrations than a non-cancerous portion of tissue. Prior to the surgical procedure, light applicator 3 is positioned against the tumor of the patient, in the pleural space for example. The light source of instrument 2 is turned on and excitation light is emitted from source emitters 21-25 to the tumor and detection fibers 26-37 collect light from areas emitting fluorescence excitation. With reference to FIG. 3, imaging system 1 can produce an image 40 from the collected light indicating the presence of cancer and location of the tumor. The absence of fluorescence excitation indicates the absence of cancer and the presence of a healthy portion of tissue. Medical personnel can use image 40 to remove the gross tumor using any known surgical procedure, including PDT. After the gross tumor has been removed, light applicator 3 is positioned against the remaining tissue of the patient in the tumor bed. If the tumor was removed using the optical light applicator as part of a PDT procedure the optical light applicator can likely remain in the same position as during the imaging procedure. The excitation light source of instrument 2 is turned on and excitation light is emitted from source emitters 21-25 to the tumor bed and detection fibers 26-37 collect light from areas emitting fluorescence excitation light which fluorescence excitation light can be indicative of cancerous cells. Because optical applicator remains positionally fixed relative to the tumor bed during the imaging process, the updated image 40 can accurately direct medical personnel to the location for subsequent procedures to remove any remaining cancerous tissue. Such a subsequent procedure can include using the therapy light source of instrument 2 to which can be configured to control the delivery of therapy light to any of the selected source emitters 21-25 in accordance with a PDT therapy plan. After any such subsequent procedures, light applicator 3 can be positioned against the remaining tissue of the patient in the tumor bed and the imaging process can be repeated to produce a subsequent digital image. Areas that emit the fluorescence excitation indicate a subsequent presence of cancer and areas that do not emit the fluorescence excitation indicate a subsequent absence of cancer. A final image can be produced and stored for future reference. In some procedures of the current disclosure using imaging system 1, a single source emitter can be turned on while using more than one (or all) of the detector fibers to produce a spatial image of the target area at an instant of time without having to move any of the optical components.

All of the methods disclosed and claimed herein can be made and executed without undue experimentation in light of the present disclosure. While the apparatus and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. In addition, modifications may be made to the disclosed apparatus and components may be eliminated or substituted for the components described herein where the same or similar results would be achieved. All such similar substitutes and modifications apparent to those skilled in the art are deemed to be within the spirit, scope, and concept of the invention.

Although the invention(s) is/are described herein with reference to specific embodiments, various modifications and changes can be made without departing from the scope of the present disclosure, as presently set forth in the claims below. Accordingly, the specification and figures are to be regarded in an illustrative rather than a restrictive sense, and all such modifications are intended to be included within the scope of the present disclosure. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise the terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

While the foregoing is directed to embodiments of the present disclosure, other and further embodiments of the disclosure may be devised without departing from the basic scope thereof, and the scope thereof is determined by the claims that follow.

What is claimed is:

1. An optical light delivery system comprising:
    an excitation light source;
    a flexible optical applicator flap having a flap length and a flap width comprised of a light transmissive material and having a plurality of longitudinal, with respect to the flap length, parallel channels distributed across the flap width of the flexible optical applicator flap and configured to be positioned against an area of tissue;
    an optical tether selectively coupled to the excitation light source and a detector;
    a plurality of source emitters each having an emitter length optically coupled to the optical tether and configured to deliver an excitation light evenly along the emitter length;
    wherein at least one of the plurality of source emitters is positioned within each of the plurality of longitudinal parallel channels and configured to deliver the excitation light along the flap length to the area of tissue;
    a plurality of detector fibers positioned proximate the plurality of source emitters optically coupled to the optical tether and configured to collect a fluorescence light from at least a portion of the area of tissue and deliver the fluorescence light to the detector; and
    a microprocessor electronically coupled to the detector and configured to produce a digital image of a cancerous tissue from the fluorescence light.

2. The optical light delivery system of claim 1 further comprising a display and wherein the display is configured to present the digital image of the cancerous tissue to a user.

3. The optical light delivery system of claim 1, wherein the excitation light source is configured to produce the excitation light at a wavelength of about 400 nm.

4. The optical light delivery system of claim 1, wherein the source emitters are cylindrical light diffusers.

5. The optical light delivery system of claim 1, wherein the detector fibers comprise isotropic probes.

6. The optical light delivery system of claim 1, further comprising:
    the area of tissue includes a photosensitizing drug and at least a portion of the area of tissue includes a plurality of cancerous cells; and
    wherein the excitation light is configured interact with the photosensitizing drug to cause the plurality of cancerous cells to produce the fluorescence light.

7. The optical light delivery system of claim 6, further comprising:
    a therapy light source optically selectively coupled to the optical tether and the source emitters and configured to produce a therapy light;
    wherein the detector fibers are further configured to collect a portion of the therapy light; and
    a controller configured to control the source emitters to produce an irradiance pattern of the therapy light based on the digital image of the cancerous tissue.

8. An interoperative light therapy method comprising:
    providing a photosensitizing drug to a tissue of a patient, wherein the photosensitizing drug is configured to concentrate in a presence of cancer in the tissue and wherein the photosensitizing drug is configured to produce a fluorescence excitation light in a presence of an excitation light;
    providing a flexible optical applicator flap having a flap length and a flap width comprised of a light transmissive material and having a plurality of longitudinal, with respect to the flap length, parallel channels distributed across the flap width of the flexible optical applicator flap;
    positioning a plurality of light emitters each having an emitter length and a plurality of detector fibers in the plurality of longitudinal parallel channels;
    positioning the flexible optical applicator flap against a target area;
    selectively coupling the plurality of light emitters to an excitation light source;
    selectively coupling the plurality of detector fibers to a detector;

emitting the excitation light evenly along the emitter length;

directing the excitation light along the flap length to a portion of the tissue in the target area of the patient; and detecting a presence or an absence of cancer in the tissue.

9. The interoperative light therapy method of claim 8 wherein the detecting the presence of cancer in a cancerous portion of the tissue comprises detecting the fluorescence excitation light and wherein the detecting the absence of cancer in a healthy portion of the tissue comprises detecting the absence of the fluorescence excitation light.

10. The interoperative light therapy method of claim 9 further comprising producing a digital image of the cancerous portion based on the fluorescence excitation light and the healthy portion based on the absence of the fluorescence excitation light.

11. The interoperative light therapy method of claim 10 further comprising resecting the cancerous portion using the digital image.

12. The interoperative light therapy method of claim 11 further comprising providing a configurable therapy light source selectively optically coupled to the plurality of light emitters and wherein the resecting the cancerous portion using the digital image comprises configuring the configurable therapy light source to direct a therapy light dosage to the cancerous portion.

13. The interoperative light therapy method of claim 12 further comprising the detecting a subsequent presence or a subsequent absence of cancer in the tissue comprising:

redirecting the excitation light to the target area of the patient; and detecting the subsequent presence of cancer based on the presence of the fluorescence excitation light and detecting the subsequent absence of cancer based on the absence of the fluorescence excitation light.

14. The interoperative light therapy method of claim 13 further comprising producing a subsequent digital image based on the presence of the fluorescence excitation light and the absence of the fluorescence excitation light.

15. An interoperative method of detecting a presence or an absence of cancer in a tissue of a patient comprising:

providing a flexible optical applicator flap having a flap length and a flap width comprised of a light transmissive material and having a plurality of longitudinal, with respect to the flap length, parallel channels distributed across the flap width of the flexible optical applicator flap;

positioning a plurality of source emitters each having an emitter length and a plurality of detector fibers in the plurality of longitudinal parallel channels;

providing an excitation light source optically coupled to the plurality of source emitters and positioning the plurality of detector fibers proximate the plurality of source emitters and optically coupled to a detector;

providing a microprocessor electronically coupled to the detector and the excitation light source;

providing a photosensitizing drug to the tissue, wherein the photosensitizing drug is configured to concentrate in the presence of cancer in the tissue and wherein the photosensitizing drug is configured to produce a fluorescence excitation light in the presence of an excitation light;

positioning the flexible optical applicator flap against an area of the tissue;

emitting an excitation light evenly along the emitter length;

delivering the excitation light along the flap length from at least one of the plurality of source emitters to an area of the tissue of the patient;

detecting the presence of cancer in a cancerous portion of the tissue by collecting the fluorescence excitation light using at least one of the plurality of detector fibers and detecting the absence of cancer in a healthy portion by the absence of collecting the fluorescence excitation light; and producing a digital image using the microprocessor of the cancerous portion based on the fluorescence excitation light and the healthy portion based on the absence of the fluorescence excitation light.

16. The interoperative method of detecting a presence or an absence of cancer in a tissue of a patient of claim 15 further comprising displaying the digital image to a user.

17. The interoperative method of detecting a presence or an absence of cancer in a tissue of a patient of claim 16 further comprising resecting the cancerous portion using the digital image.

18. The interoperative method of detecting a presence or an absence of cancer in a tissue of a patient of claim 17 further comprising:

providing a configurable therapy light source and wherein the resecting the cancerous portion using the digital image comprises configuring the configurable therapy light source to direct a therapy light dosage to the cancerous portion.

19. The interoperative method of detecting a presence or an absence of cancer in a tissue of a patient of claim 18 further comprising detecting a subsequent presence or a subsequent absence of cancer in the tissue comprising:

redirecting the excitation light to the area of the patient; and detecting the subsequent presence of cancer based on the presence of the fluorescence excitation light and detecting the subsequent absence of cancer based on the absence of the fluorescence excitation light.

20. The interoperative method of detecting a presence or an absence of cancer in a tissue of a patient of claim 19 further comprising producing a subsequent digital image based on the presence of the fluorescence excitation light and the absence of the fluorescence excitation light.

21. The interoperative method of detecting a presence or an absence of cancer in a tissue of a patient of claim 15, the excitation light source producing the excitation light at a wavelength of about 400 nm.

* * * * *